_United States Patent_ [19]

Leistner et al.

[11] Patent Number: 4,463,112

[45] Date of Patent: Jul. 31, 1984

[54] PHENYLETHYLIDENE-SUBSTITUTED PHENYL POLYPHOSPHITES

[76] Inventors: William E. Leistner, 1458 Bay Blvd., Atlantic Beach, N.Y. 11509; Motonobu Minagawa, 1-207-3 Shichizacho, Koshigaya, Japan; Yutaka Nakahara, 406-71, Minamishimoarai, Iwatsuki, Saitama, Japan; Kazumi Kitsukawa, 3-12, Hikonari, Misato, Saitama, Japan

[21] Appl. No.: 121,133

[22] Filed: Feb. 13, 1980

[51] Int. Cl.$^3$ ................................................ C08K 5/52
[52] U.S. Cl. .................................... 524/109; 524/118; 524/120; 524/128; 524/305; 524/350; 525/150; 525/437; 525/538
[58] Field of Search ............... 260/45.7 PH;45.8 R, 260/45.95 H, 930, 45.8 AH; 524/118, 120, 128

[56] References Cited

U.S. PATENT DOCUMENTS

| | | | |
|---|---|---|---|
| 2,471,887 | 5/1949 | Nelson | 260/45.95 H |
| 3,127,369 | 3/1964 | Warren | 260/45.8 R |
| 3,192,243 | 6/1965 | Gagliani | 260/45.8 R |
| 3,231,531 | 1/1966 | Buckley et al. | 260/45.75 W |
| 3,245,926 | 4/1966 | Parker | 260/45.8 R |
| 3,245,979 | 4/1966 | Nelson et al. | 260/930 |
| 3,356,770 | 12/1967 | Larrison | 260/930 |
| 3,454,523 | 7/1969 | Tholstrup | 260/45.8 R |
| 3,484,506 | 12/1969 | Baranauckas et al. | 260/930 |
| 3,856,728 | 12/1974 | Abramoff | 260/45.8 AH |
| 3,940,367 | 2/1976 | Pelousek et al. | 260/45.7 PH |
| 4,233,208 | 11/1980 | Spivack | 260/45.7 PH |
| 4,261,880 | 4/1981 | Fujii et al. | 260/45.8 R |

_Primary Examiner_—John Kight, III
_Assistant Examiner_—R. A. White

[57] ABSTRACT

Organic polyphosphites are disclosed having in the molecule at least two phosphite ester groups, at least one of which is linked through oxygen to a phenylethylidene-substituted phenyl group and to a residue of a polyhydroxy compound which is a pentaerythritol residue or a residue of a phenol or alcohol having two to three hydroxyl groups separated from one another by at least three carbon atoms.

Polymer stabilizer compositions comprising an organic polyphosphite as disclosed and a known polymer stabilizer, as well as synthetic resin stabilized with such stabilizer compositions, are also disclosed.

19 Claims, No Drawings

PHENYLETHYLIDENE-SUBSTITUTED PHENYL POLYPHOSPHITES

This invention relates to stabilized polymer composition comprising (α-methyl)styrenated phenyl polyphosphite compounds. In the formula (I) and (II), alkyl include methyl, ethyl, propyl, iso-propyl, butyl, sec-butyl, t-butyl, amyl, t-amyl, iso-amyl, hexyl, iso-hexyl, heptyl, octyl, iso-octyl, 2-ethylhexyl, t-octyl, decyl, iso-decyl, lauryl, tridecyl, $C_{12-13}$ mixed alkyl, stearyl, cyclopentyl, cyclohexyl, cyclooctyl, cyclododecyl and 4-methylcyclohexyl; arylalkyl include benzyl, 1-phenylethyl, 2-phenylethyl, 1-phenyl-1-methyl-ethyl, 2-phenylpropyl and 3-phenylpropyl; alkyl containing ether linkage include furfuryl, tetrahydrofurfuryl, 5-methylfurfuryl, α-methylfurfuryl, residual group of methyl-, ethyl-, isopropyl-, butyl-, iso-butyl-, hexyl-, cyclohexyl- or phenyl-Cellosolve, residual group of methyl-, ethyl-, iso-propyl-, butyl- or iso-butyl-Carbitol, residual group of triethyleneglycol-monomethylether, -monoethylether or -monobutylether, residual group of glycerin-1,2-dimethylether, -1,3-dimethylether, -1,3-diethylether or -1-ethyl-2-propylether, nonylphenoxypolyethoxyethyl and lauroxypolyethoxyethyl; aryl include phenyl, phenylphenyl and naphthyl; alkylaryl include tolyl, xylyl, ethylphenyl, butylphenyl, t-butylphenyl, octylphenyl, isooctylphenyl, t-octylphenyl, nonylphenyl, 2,4-di-t-butylphenyl, cyclohexylphenyl and cyclooctylphenyl; alkoxy include methoxy, ethoxy and propoxy; halogen include chlorine and bromine. Di or tri hydric phenol of $A+OH)_{2+m}$ include hydroquinone, 2,5-di-t-butylhydroquinone, 2,3,6-trimethylhydroquinone, 2-methyl resorcin, 2,6-di-t-butylresorcin, 2,2'-methylene bis(4-methyl-6-t-butylphenol), 2,2'-methylene bis-4-ethyl-6-t-butyl, 2,2'-methylenebis [4-methyl-6-(α-methylcyclohexyl)phenol], 2,2'-n-butylidenebis(4,6-dimethylphenol), 1,1-bis(2'-hydroxy-3',5'-dimethylphenyl)-3,5,5-trimethylhexane, 2,2'-cyclohexylidenebis(4-ethyl-6-t-butylphenol), 2,2'-iso-propylbenzylidenebis(4-ethyl-6-t-butylphenol), 2,2'-thiobis(4-t-butyl-6-methylphenol), 2,2'-thiobis(4-methyl-6-t-butylphenol), 2,2'-thiobis(4,6-di-t-butylphenol), 4,4'-methylenebis(2-methyl-6-t-butylphenol), bisphenol A, 4,4'-isopropylidenebis(2-phenylethylphenol), 4,4'-n-butylidenebis(3-methyl-6-t-butylphenol), 4,4'-cyclohexylidenebisphenol, 4,4'-cyclohexylidenebis(2-t-butylphenol), 4,4'-cyclohexylidenebis(2-cyclohexylphenol), 4,4'-benzylidenebis(2-t-butyl-5-methylphenol), 4,4'-oxobis(3-methyl-6-isopropylphenyl), 4,4'-thiobis(3-methyl-6-t-butylphenol), 4,4'-sulfobis(3-methyl-6-t-butylphenol), bis(2-methyl-4-hydroxy-5-t-butylbenzyl)sulfide, 1,1,3-tris(2'-methyl-4'-hydroxy-5'-t-butylphenyl)butane and 2,2-bis(3'-t-butyl-4'-hydroxyphenyl)-4-(3'',5''-di-t-butyl-4''-hydroxyphenyl)butane. Di or tri hydric alcohol of $A+OH)_{2+m}$ include ethyleneglycol, diethyleneglycol, triethyleneglycol, 1,2-propanediol, 1,3-propanediol, 1,2-butanediol, 1,3-butanediol, 1,4-butanediol, neopentylglycol, thiodiethyleneglycol, 1,6-hexanediol, 1,10-decanediol, 1,4-cyclohexanediol, 1,4-cyclohexanedimethanol, 1,4-benzenedimethanol, hydrogenatedbisphenol A, glycerin, trimethylolethane, trimethylolpropane and tris(2-hydroxyethyl)isocyanurate.

The typical examples of compounds of formula (I) and (II) are shown below.

No. 1  Tetra[2,4-di-(1-phenylethyl)phenyl].hydroquinone.diphosphite

No. 2  Bis[2,4-di-(1-phenylethyl)phenyl].didodecyl.hydroquinone.diphosphite

No. 3  Bis[2-(2-phenylisopropyl)-4-t-butylphenyl].bis(2,4-di-t-butylphenyl).2,5-di-t-butylhydroquinone diphosphite No. 4  Bis[2-(1-phenylethyl)4-methoxyphenyl].di(tridecyl).2,5-di-t-butylhydroquinone.diphosphite No. 5  Bis[2-(2-phenylisopropyl)-4-t-butylphenyl]bis(hydrogenated bisphenol A).bisphenol A.diphosphite No. 6  Bis[2-(1-phenylethyl)-4,6-dimethylphenyl].dihydrogen.bisphenol A.diphosphite No. 7  2,4,6-Tris(1-phenylethyl)phenyl.tri(isooctyl).bisphenol A.diphosphite No. 8  Bis[2,4-di-(2-phenylisopropyl)phenyl].di($C_{12-15}$ mixed alkyl).bisphenol A.diphosphite No. 9  Bis[2-(1-phenylethyl)-4-nonylphenyl].diphenyl.bisphenol A.diphosphite No. 10  Tris[2-(2-phenylisopropyl)-4-methylphenyl].di(tridecyl).di(bisphenol A).triphosphite No. 11  Bis[2-(2-phenylisopropyl)-4-octylphenyl].di(octadecyl).4,4'-butylidenebis(2-t-butyl-5-methylphenol).diphosphite No. 12  Bis[2-(1-phenylethyl)-4-chlorophenyl].dibenzyl.4,4'-butylidenebis(2-t-butyl-5-methylphenol).diphosphite No. 13  Tris[2-(1-phenylethyl)phenyl].(tridecyl).4,4'-butylidenebis(2-t-butyl-5-methylphenol).diphosphite No. 14  Tetra[2,4-di-(1-phenylethyl)phenyl].4,4'-cyclohexylidenediphenol.diphosphite No. 15  Bis[2-(1-phenylethyl)-4-phenylphenyl].di(isodecyl).4,4'-sulfobisphenol.diphosphite No. 16  Tris[2-(2-phenylisopropyl)-4-t-butylphenyl].hydrogen.4,4'-thiobis(2-t-butyl-5-methylphenol).diphosphite No. 17  Bis[2-(2-phenylisopropyl)-4-methylphenyl].tri(4,4'-methylenebisphenol).diphosphite No. 18  Bis[2,4-di-(1-phenylethyl)phenyl].di(ethoxyethyl).4,4'-thiobisphenol.diphosphite No. 19  Tetra[2,4-di-(2-phenylisopropyl)phenyl].1,1,3-tris(2-methyl-4-hydroxy-5-t-butylphenyl)butane.diphosphite No. 20  Hexa[2,4-di-(1-phenylethyl)-6-methylphenyl].1,1,3-tris(2-methyl-4-hydroxy-5-t-butylphenyl)butane triphosphite No. 21  Tetra[2,4-di-(1-phenylethyl)-5-methylphenyl].neopentylglycol.diphosphite No. 22  Bis[2-(2-phenylisopropyl)phenyl].diphenyl.neopentylglycol.diphosphite No. 23  Tetra[2-(1-phenylethyl)-4-cyclohexylphenyl].diethyleneglycol.diphosphite No. 24  Tetra[2-(2-phenylisopropyl)-4-t-butylphenyl].tetrapropyleneglycol.diphosphite No. 25  Tetra[2,4-di-(1-phenylethyl)phenyl].pentapropyleneglycol.diphosphite No. 26  Bis[2-(2-phenylisopropyl)-4-methylphenyl].di(isooctyl).1,6-hexanediol.diphosphite No. 27  Tetra[2-(2-phenylisopropyl)-4-t-butylphenyl].1,10-decanediol.diphosphite No. 28  Bis[2,4-di-(1-phenylethyl)phenyl].1,10-decanediol.diphenyl.diphosphite No. 29  Bis[2-(2-phenylisopropyl)-4-methylphenyl].bis(butoxyethoxyethyl).hydrogenated bisphenol A.diphosphite No. 30  Tetra[2-(2-phenylisopropyl)-4-methylphenyl].diphenyl.tri(hydrogenatedbisphenol A).tetraphosphite No. 31 Tetra[2,4-di-(1-phenylethyl)phenyl].hydrogenatedbisphenol A.diphosphite No. 32 Bis[2-(2-phenylisopropyl)-4-t-butylphenyl].dihydrogen.hydrogenatedbisphenol A.diphosphite No. 33 Tris[2-(1-phenylethyl)-4-methylphenyl].di(tridecyl).di(hydrogenatedbisphenol A).triphosphite No. 34 Tetra[2,4-di-(2-phenylisoproypyl)phenyl].1,4-cyclohexanedimethanol.diphosphite No. 35 Bis[2-(2-phenylsiopropyl)-4-methylphenyl].di(isodecyl).1,4-cyclohexanedimethanol.diphosphite No. 36 Bis[2-(2-phenylisopropyl)-4-cyclohexylphenyl].dicyclohexyl.1,4-cyclohexanedimethanol.diphosphite No. 37 Hexa[2-(1-phenylethyl)-4-methylphenyl].tris(2-hydroxyethyl)isocyanurate.triphosphite No. 38 Tris[2-(1-phenylethyl)-4-octylphenyl].tri(tridecyl).tris(2-hydroxyethyl)isocyanurate.triphosphite No. 39 Tetra[2,4-di-(1-phenylethyl)phenyl].tetra(isodecyl).phenyl.di[tris(2-hydroxyethyl)isocyanurate].pentaphosphite No. 40 Bis[2,4-di-(1-phenylethyl)phenyl].pentaerythritol.diphosphite No. 41 Bis[2-(2-phenylisopropyl)-4-octylphenyl].pentaerythritol.diphosphite No. 42 2-(2-Phenylisopropyl)-4-t-butylphenyl.2,4-di-t-butylphenyl.pentaerythritol.diphosphite No. 43 2-(2-Phenylisopropyl)-4-methylphenyl.octadecyl.pentaerythritol.diphosphite No. 44 2-(1-phenylethyl)-4-methylphenyl.bisphenol A.pentaerythritol.diphosphite No. 45 2,4-di-(1-phenylethyl)phenyl.hydrogen.pentaerythritol.diphosphite Phosphite compounds of formula (I) or (II) were easily prepared by reacting di or tri hydric phenol or alcohol of A-(OH)$_{2+m}$, (α-methyl)styrenated phenol of

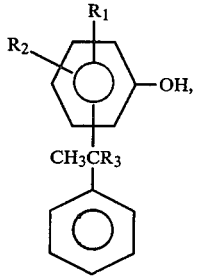

R$_4$OH, R$_5$OH and R$_6$OH with phosphorous trichloride, triphenylphosphite or trimethylphosphite or reacting pentaerythritol, (α-methyl)styrenated phenol and R$_4$OH with phosphorous trichloride, triphenylphosphite or trimethylphosphite and, if desired, hydrolysis the phosphite.

SYNTHETIC EXAMPLE 1 (SYNTHESIS OF NO. 10 COMPOUND)

Triphenylphosphite 46.5 g (0.15 mole), bisphenol A 22.8 g (0.1 mole), 2-(2-phenylisopropyl)-4-methylphenol 33.9 g (0.15 mole) tridecanol 20.0 g (0.1 mole), and K$_2$CO$_3$ 0.1 g were heated at 150° C. for 3 hrs. under nitrogen stream and then phenol was distilled at 160° C./3 mmHg. After cooling, colorless glassy solid product was obtained.

SYNTHESIS EXAMPLE 2 (SYNTHESIS OF NO. 29 COMPOUND)

Triphenylphosphite 31.0 g (0.1 mole), hydrogenated bisphenol A 12.0 g (0.05 mole) and K$_2$CO$_3$ 0.05 g were heated at 150° C. for 3 hrs. under nitrogen stream, and then produced phenol was distilled. Then, 2-(2-phenylisopropyl)-4-methylphenol 22.6 g (0.1 mole), butoxyethoxyethanol 16.2 g (0.1 mole) and K$_2$CO$_3$ 0.7 g were added and heated at 150° C. for 3 hrs. under nitrogen stream, then phenol was distilled and viscous liquid product was obtained.

SYNTHETIC EXAMPLE 3 (SYNTHESIS OF NO. 41 COMPOUND)

Triphenyl phosphite 31.0 g (0.1 mole), pentaerythritol 6.8 g (0.05 mole), 2-(2-phenylisopropyl)-4-octylphenol 32.4 g (0.1 mole) and K$_2$CO$_3$ 0.07 g were heated at 150° C. for 3 hrs. under nitrogen stream, then produced phenol was distilled and colorless glassy solid product was obtained.

Known auxiliary stabilizers can be employed in polymer composition of this invention. Such stabilizers include metal salts of carboxylic acid or phenols, phenolic antioxidants, epoxy compounds, light stabilizers and thioether compounds.

EXAMPLE 1

A sheet of 1 mm thick was prepared by kneading polyvinylchloride resin (Geon 103EP) 100 parts, dioctylphthalate 42 parts, epoxidized soybean oil 2 parts, calcium stearate 1.0 part, zinc stearate 0.2 part and phosphite compound 0.5 part on a two roll mill. Then, heat stability test was carried out in a Geer oven at 190° C., initial color of sheet was measured by Hunter colorimeter and expressed in terms of yellowness and clarity of sheet was determined.

TABLE - 1

| No. | Phosphite compound | Heat Stability min | Yellowness | Clarity |
|---|---|---|---|---|
| Control | | | | |
| 1-1 | None | 35 | 35 | little inferior |
| 1-2 | Octyl.diphenylphosphite | 45 | 31 | medium |
| 1-3 | Tris[2,4-di-(2-phenylisopropyl)phenyl] phosphite | 40 | 33 | " |
| 1-4 | Tetra(tridecyl).2,5-di-t-butylhydroquinone. diphosphite | 50 | 28 | " |
| Example | | | | |
| 1-1 | No. 1 | 85 | 14 | much superior |
| 1-2 | No. 4 | 95 | 13 | much superior |
| 1-3 | No. 8 | 95 | 12 | much superior |
| 1-4 | No. 12 | 80 | 16 | superior |
| 1-5 | No. 17 | 85 | 14 | " |
| 1-6 | No. 20 | 90 | 15 | much superior |
| 1-7 | No. 24 | 80 | 13 | much superior |
| 1-8 | No. 28 | 85 | 12 | superior |
| 1-9 | No. 32 | 100 | 15 | much superior |
| 1-10 | No. 37 | 90 | 14 | much superior |
| 1-11 | No. 42 | 85 | 15 | much |

TABLE - 1-continued

| No. | Phosphite compound | Heat Stability min | Yellow-ness | Clarity |
|---|---|---|---|---|
| | | | | superior |

EXAMPLE 2

In order to examine the effect of this invention in rigid PVC composition, test pieces were prepared by the same procedure as in Example 1 in accordance with the following formulation. Then, heat stability test at 190° C. was carried out, initial color was measured and plate out value was determined according to Watchung-red method.

The results are shown in Table 2.

(Formulation)

| PVC (Geon 103EP8) | 100 parts |
|---|---|
| Epoxydized linseed oil | 2.0 |
| Mg-stearate | 0.2 |
| Ca-stearate | 1.0 |
| Zn-stearate | 0.4 |
| Phosphite compound | 0.7 |

TABLE - 2

| No. | Phosphite compound | Heat Stability min | Initial Color | Plate Out Value |
|---|---|---|---|---|
| Control | | | | |
| 2-1 | Tris(nonylphenyl) phosphite | 45 | 24 | 80 |
| 2-2 | Tetraphenyl.bisphenol A. diphosphite | 50 | 22 | 70 |
| 2-3 | 2-(1-Phenylethyl)-4-methylphenyl.di(isodecyl). phosphite | 50 | 21 | 55 |
| Example | | | | |
| 2-1 | No. 2 | 80 | 14 | 20 |
| 2-2 | No. 6 | 90 | 11 | 30 |
| 2-3 | No. 10 | 90 | 12 | 15 |
| 2-4 | No. 14 | 85 | 11 | 20 |
| 2-5 | No. 18 | 80 | 13 | 25 |
| 2-6 | No. 21 | 95 | 13 | 25 |
| 2-7 | No. 26 | 90 | 12 | 30 |
| 2-8 | No. 30 | 95 | 14 | 20 |
| 2-9 | No. 35 | 90 | 11 | 20 |
| 2-10 | No. 39 | 85 | 13 | 15 |
| 2-11 | No. 44 | 80 | 15 | 25 |

EXAMPLE 3

In order to examine the effect of this invention in PVC-ABS resin blend, a sheet was prepared in accordance with following formulation, and then heat stability test was carried out at 175° C.

The results are shown in Table 3.

(Formulation)

| PVC (Geon 103EP8) | 100 parts |
|---|---|
| ABS (Blendex 111) | 10 |
| Epoxydized soybean oil | 1.0 |
| Stearic acid | 0.3 |
| Ba-nonylphenate | 0.7 |
| Zn-toluate | 0.4 |
| Phosphite compound | 0.5 |

TABLE - 3

| No. | Phosphate compound | Heat Stability min |
|---|---|---|
| Control | | |
| 3-1 | None | 45 |
| 3-2 | Tris[2,4-di-(1-phenylethyl)phenyl] phosphite | 55 |
| Example | | |
| 3-1 | No. 4 | 105 |
| 3-2 | No. 9 | 95 |
| 3-3 | No. 13 | 90 |
| 3-4 | No. 16 | 100 |
| 3-5 | No. 19 | 95 |
| 3-6 | No. 25 | 85 |
| 3-7 | No. 30 | 90 |
| 3-8 | No. 34 | 90 |
| 3-9 | No. 38 | 95 |
| 3-10 | No. 41 | 100 |
| 3-11 | No. 45 | 85 |

EXAMPLE 4

A sheet was prepared in accordance with following formulation, then heat stability test was carried out 190° C., initial color was measured and weatherability test was carried out in a Weather-O-Meter.

The results are shown in Table 4.

(Formulation)

| PVC (Vinica 37H) | 100 parts |
|---|---|
| DOP | 45 |
| Tricresylphosphate | 5 |
| Bisphenol A.diglycidylether | 3 |
| Diphenyl.hydrogenphosphite | 0.3 |
| Zn-stearate | 0.8 |
| Ba-stearate | 0.4 |
| Ba-nonylphenate | 0.5 |
| Sorbitan monopalmitate | 1.0 |
| Phosphite compound | 0.5 |

TABLE - 4

| No. | Phosphite compound | Heat Stability min | Initial Color | Weather ability hrs |
|---|---|---|---|---|
| Control | | | | |
| 4-1 | None | 50 | 28 | 500 |
| 4-2 | Bis[2-(1-phenylethyl)-4-methylphenyl] .isodecyl-phosphite | 65 | 25 | 800 |
| 4-3 | Tetradodecyl.hydroquinone.diphosphite | 60 | 25 | 700 |
| Example | | | | |
| 4-1 | No. 2 | 100 | 13 | 1200 |
| 4-2 | No. 3 | 100 | 12 | 1500 |
| 4-3 | No. 7 | 95 | 12 | 1300 |
| 4-4 | No. 11 | 90 | 15 | 1300 |
| 4-5 | No. 15 | 90 | 13 | 1200 |
| 4-6 | No. 22 | 100 | 14 | 1400 |
| 4-7 | No. 27 | 95 | 13 | 1300 |
| 4-8 | No. 31 | 105 | 12 | 1500 |
| 4-9 | No. 36 | 95 | 15 | 1400 |
| 4-10 | No. 40 | 90 | 14 | 1300 |

EXAMPLE 5

In order to examine the effect of combination of epoxy compound with phosphite compound of this invention, a sheet was prepared in accordance with following formulation. Then same tests as in Example 1 were carried out.

The results are shown in Table 5.

| (Formulation) | |
|---|---|
| PVC (Geon 103EP) | 100 parts |
| DOP | 50 |
| Stearic acid | 0.3 |
| Zn-octoate | 0.3 |
| Ba-neodecanoate | 0.7 |
| Phosphite compound No. 8 | 0.4 |
| Epoxy compound | 1.0 |

TABLE - 5

| No. | Epoxy compound | Heat Stability min | Initial Color | Clarity |
|---|---|---|---|---|
| Control | | | | |
| 5-1 | None (without phosphite) | 45 | 28 | inferior |
| 5-2 | Epoxidized soybean oil 1.4 (without phosphite) | 55 | 23 | little inferior |
| Example | | | | |
| 5-1 | None | 90 | 14 | superior |
| 5-2 | Epoxidized soybean oil | 120 | 10 | much superior |
| 5-3 | Epoxidized linseed oil | 125 | 10 | much superior |
| 5-4 | Epoxidized polybutadiene | 105 | 13 | much superior |
| 5-5 | Tris(epoxypropyl)isocyanurate | 110 | 13 | much superior |
| 5-6 | Bisphenol A.diglycidylether | 120 | 12 | much superior |
| 5-7 | Vinylcyclohexenediepoxide | 105 | 12 | much superior |
| 5-8 | 3-(2-Xenoxy)-1,2-epoxypropane | 110 | 13 | much superior |
| 5-9 | Octylepoxystearate | 120 | 11 | much superior |
| 5-10 | 3,4-Epoxycyclohexylmethyl-3,4-epoxycyclohexane-carboxylate | 110 | 12 | much superior |

EXAMPLE 6

Pellets were prepared by extruding following formulation at 230° C. The pellets were then injection molded at 230° C. to prepare test pieces of 2 mm thick. And another test pieces were prepared from the pellets after retained for 10 minutes and 20 minutes in injection machine. Then color of test pieces was measured by a Hunter colorimeter and shown as yellowness. The results are shown in Table 6.

| (Formulation) | |
|---|---|
| Styrene-acrylonitrile copolymer | 100 parts |
| 2,2'-Methylenebis(4-methyl-6-t-butylphenol) | 0.05 |
| Phosphite compound | 0.05 |

TABLE - 6

| No. | Phosphite compound | Original | Yellowness after 10 min | after 20 min |
|---|---|---|---|---|
| Control | | | | |
| 6-1 | Tris[2,4-di-(1-phenylethyl)phenyl]phosphite | 13 | 16 | 23 |
| 6-2 | Tris[2-(2-phenylisopropyl)-4-methylphenyl]phosphite | 12 | 17 | 26 |
| Example | | | | |
| 6-1 | No. 1 | 11 | 13 | 17 |
| 6-2 | No. 5 | 10 | 13 | 16 |
| 6-3 | No. 11 | 8 | 10 | 14 |
| 6-4 | No. 16 | 10 | 12 | 15 |
| 6-5 | No. 19 | 8 | 11 | 15 |
| 6-6 | No. 23 | 11 | 13 | 16 |
| 6-7 | No. 29 | 9 | 12 | 16 |
| 6-8 | No. 33 | 10 | 12 | 15 |
| 6-9 | No. 39 | 10 | 14 | 17 |
| 6-10 | No. 43 | 9 | 11 | 15 |

EXAMPLE 7

Pellets were prepared by extruding following formulation and the pellets were injection molded at 230° C. to prepare test pieces. The color of test pieces after heating at 135° C. for 30 hrs. in a Geer oven was measured and shown as whiteness. Izod impact strength of test pieces at 20° C. was determined and izod impact strength of test pieces after immersion in water of 100° C. for 72 hrs. was also determined.

The results are shown in Table 7.

| (Formulation) | |
|---|---|
| ABS resin (Styrac 200) | 100 parts |
| TiO$_2$ | 2.0 |
| Ca-stearate | 1.0 |
| 4,4'-Butylidenebis(2-t-butyl-5-methylphenol) | 0.1 |
| Phosphite compound | 0.3 |

TABLE - 7

| No. | Phosphtie compound | Whiteness | Izod impact strength (kg · cm/cm) original | after heating | after immersed |
|---|---|---|---|---|---|
| Control | | | | | |
| 7-1 | None | 13.4 | 13.5 | 10.2 | 13.0 |
| 7-2 | Tris[2,4-di-(1-phenylethyl)phenyl]phosphite | 16.5 | 18.4 | 14.3 | 15.6 |
| 7-3 | Tetraphenyl.4,4'-thiobisphenol.diphosphite | 15.0 | 18.5 | 14.1 | 14.3 |
| Example | | | | | |
| 7-1 | No. 3 | 33.6 | 18.7 | 16.2 | 18.1 |
| 7-2 | No. 7 | 35.4 | 18.8 | 16.5 | 18.3 |
| 7-3 | No. 13 | 36.0 | 19.1 | 16.8 | 18.6 |
| 7-4 | No. 15 | 33.8 | 18.5 | 16.3 | 17.7 |
| 7-5 | No. 18 | 34.6 | 18.8 | 16.6 | 18.0 |
| 7-6 | No. 20 | 35.5 | 19.2 | 16.7 | 18.4 |
| 7-7 | No. 22 | 34.4 | 18.5 | 16.0 | 17.9 |
| 7-8 | No. 28 | 35.2 | 18.9 | 16.5 | 18.0 |
| 7-9 | No. 33 | 35.7 | 18.6 | 16.2 | 17.9 |
| 7-10 | No. 37 | 32.4 | 19.0 | 17.0 | 18.3 |
| 7-11 | No. 42 | 35.3 | 18.9 | 16.7 | 18.1 |

EXAMPLE 8

Following formulation were blended in a mixer and then extruded to prepare compound. Then, a sheet of 95×40×1 mm was injection molded. The heat stability test at 160° C. was carried out in a Geer oven and color of sheet was measured and shown as yellowness.

The results are shown in Table 8.

| (Formulation) | |
|---|---|
| Polypropylene (Profax 6501) | 100 parts |
| Ca-stearate | 0.2 |
| Dilaurylthiodipropionate | 0.2 |
| Pentaerythritoltetrakis | 0.1 |

-continued

| (Formulation) | |
|---|---|
| (3,5-di-t-butyl-4-hydroxyphenyl propionate) | |
| Phosphite compound | 0.1 |

TABLE - 8

| No. | Phosphite compound | Heat Stability hrs | Yellowness |
|---|---|---|---|
| Control | | | |
| 8-1 | None | 355 | 12.1 |
| 8-2 | Tris[2,4-di-(2-phenylisopropyl)phenyl]phosphite | 405 | 10.5 |
| Example | | | |
| 8-1 | No. 5 | 820 | 7.4 |
| 8-2 | No. 12 | 855 | 7.3 |
| 8-3 | No. 14 | 790 | 8.0 |
| 8-4 | No. 19 | 835 | 7.7 |
| 8-5 | No. 24 | 775 | 7.8 |
| 8-6 | No. 27 | 815 | 7.4 |
| 8-7 | No. 31 | 805 | 7.6 |
| 8-8 | No. 35 | 830 | 7.5 |
| 8-9 | No. 38 | 845 | 7.5 |
| 8-10 | No. 41 | 820 | 7.8 |
| 8-11 | No. 44 | 835 | 7.3 |

EXAMPLE 9

Polyethylene resin (Hizex 5100E) 100 parts, distearylthiodipropionate 0.3 part, stearyl-3,5-di-t-butyl-4-hydroxyphenylpropionate 0.1 part and phosphite compound 0.1 part were mixed for 5 minutes at 150° C. on a roll mill, followed by compression molding at 150° C. and 180 kg/cm² for 5 minutes, to obtain a sheet of 1.0 mm in thickness. Test pieces of 10×20 mm were cut off from the sheet and heat stability test was carried out at 150° C. in a Geer oven on alminum foil.

The results are shown in Table 9.

TABLE - 9

| No. | Phosphite compound | Heat Stability hrs |
|---|---|---|
| Control | | |
| 9-1 | None | 280 |
| 9-2 | Tris(nonylphenyl)phosphite | 330 |
| 9-3 | Tetraoctyl.2,5-di-t-butylhydroquinon.diphosphite | 425 |
| Example | | |
| 9-1 | No. 3 | 585 |
| 9-2 | No. 9 | 550 |
| 9-3 | No. 13 | 600 |
| 9-4 | No. 20 | 590 |
| 9-5 | No. 26 | 545 |
| 9-6 | No. 29 | 565 |
| 9-7 | No. 34 | 560 |
| 9-8 | No. 40 | 590 |
| 9-9 | No. 43 | 580 |

EXAMPLE 10

Poly(2,6-dimethyl-1,4-phenyleneoxide) of internal viscosity 0.56 dl/g (in chloroform at 25° C.) 50 parts, polystyrene 47.5 parts, polycarbonate 2.5 parts and phosphite compound 0.5 part were mixed by mixer and extruded to prepare pellets, followed by injection molding to obtain test pieces. The test pieces was heated at 125° C. for 100 hours in a Geer oven and elongation retained and izod impact strength retained were determined.

The results are shown in Table 10.

TABLE - 10

| | | Retention (%) | |
|---|---|---|---|
| No. | Phosphite compound | Elongation | Izod impact strength |
| Control | | | |
| 10-1 | Tridecylphosphite | 32 | 40 |
| 10-2 | Tetra(tridecyl). bisphenol A.diphosphite | 35 | 43 |
| Example | | | |
| 10-1 | No. 6 | 63 | 72 |
| 10-2 | No. 10 | 65 | 73 |
| 10-3 | No. 12 | 60 | 68 |
| 10-4 | No. 25 | 61 | 66 |
| 10-5 | No. 36 | 63 | 69 |
| 10-6 | No. 38 | 62 | 70 |
| 10-7 | No. 41 | 66 | 73 |

EXAMPLE 11

Polycarbonate 100 parts and phosphite 0.2 part were compression molded at 260° C. to prepare a sheet of 1 mm in thickness. The color of sheet after heated at 230° C. for 30 minutes in a Geer oven was determined.

The results are shown in Table 11.

TABLE - 11

| No. | Phosphite compound | Color of sheet |
|---|---|---|
| Control | | |
| 11-1 | None | Dark brown |
| 11-2 | Distearyl.pentaerythritol. diphosphite | Light brown |
| Example | | |
| 11-1 | No. 5 | Colorless |
| 11-2 | No. 11 | " |
| 11-3 | No. 17 | Pale yellow |
| 11-4 | No. 21 | Colorless |
| 11-5 | No. 23 | Pale yellow |
| 11-6 | No. 32 | Colorless |
| 11-7 | No. 40 | " |
| 11-8 | No. 45 | " |

We claim:

1. A synthetic resin composition having enhanced resistance to deterioration on exposure to heat and light comprising a synthetic resin selected from the group consisting of ethylene-vinyl acetate copolymers, alkanediolterephthalate linear polyesters, polyvinyl chloride, and ABS polymer, and a polyphosphite ester represented by formula (I) or formula (II)

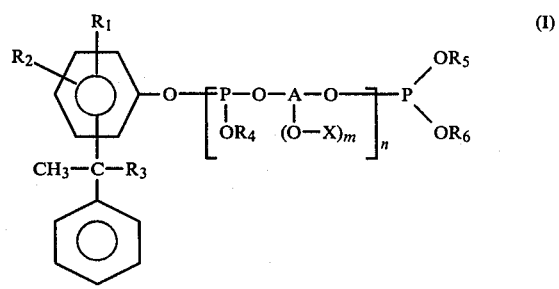

-continued

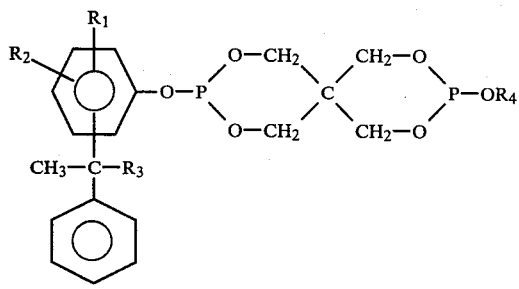

(II)

in which each of $R_1$ and $R_2$ is selected from the group consisting of hydrogen, alkyl and alkoxy having from one to ten carbon atoms, aryl having from six to fourteen carbon atoms, alkaryl and aralkyl having from seven to twenty-four carbon atoms, and halogen; $R_3$ is hydrogen or methyl; and each of $R_4$, $R_5$ and $R_6$ is selected from the group consisting of hydrogen, alkyl and cycloalkyl having from six to twenty carbon atoms, aryl having six to fourteen carbon atoms, alkaryl and aralkyl having from seven to twenty-four carbon atoms, ether-linked groups having from three to seventy-five carbon atoms and from one to thirty ether oxygen atoms, and —A—$(OH)_{m+1}$ in which m is 0 or 1; n is a number from 1 to 10; A is a residue of a phenol or alcohol having from two to three hydroxy groups, and X is hydrogen or —P(—$OR_5$)$OR_6$, and a synthetic resin stabilizer selected from the group consisting of phenolic antioxidants, thioether sulfur antioxidants, organic phosphites having one phosphite group, epoxidized oils, and monocarboxylic acid salts of Group II metals.

2. A synthetic resin composition according to claim 1 in which the synthetic resin is polybutylene terephthalate.

3. A synthetic resin composition according to claim 1 in which the synthetic resin is polyvinyl chloride.

4. A synthetic resin composition according to claim 1 in which the synthetic resin is ABS polymer.

5. A synthetic resin composition according to claim 1 in which the synthetic resin stabilizer is 2,6-di-t-butyl-p-cresol.

6. A synthetic resin composition according to claim 1 in which the synthetic resin stabilizer is dilauryl thiodipropionate.

7. A synthetic resin composition according to claim 1 in which the synthetic resin stabilizer is distearyl thiodipropionate.

8. A synthetic resin composition according to claim 1 in which the synthetic resin stabilizer is epoxidized soybean oil.

9. A synthetic resin composition according to claim 1 in which the polyphosphite ester has from two to ten phosphite groups in a linear chain.

10. A synthetic resin composition according to claim 1 in which the polyphosphite ester is a cross-linked polymer.

11. A synthetic resin composition according to claim 1 in which $R_3$ is a methyl group.

12. A synthetic resin composition according to claim 1 in which $R_4$ and $R_5$ are each hydrogen.

13. A synthetic resin composition according to claim 1 in which $R_4$ and $R_5$ are each phenylethylidene groups represented by Formula III

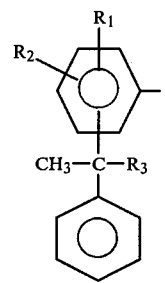

14. A synthetic resin composition according to claim 1 in which $R_4$ and $R_5$ are each an alkyl group having from six to twenty carbon atoms.

15. A synthetic resin composition according to claim 1 in which A is a 1,4-phenylene group.

16. A synthetic resin composition according to claim 1 in which A is an alkylene group having from four to twelve carbon atoms.

17. A synthetic resin composition according to claim 1 in which A is a residue of a polycyclic dihydric or trihydric phenol having two non-condensed benzenoid rings connected by a linking group which is a single bond, sulfur or oxygen, hydrocarbon having from one to twenty carbon atoms, arylalkylidene, or a hydroxyaryl-substituted hydrocarbon group.

18. A synthetic resin composition according to claim 1 in which the polyphosphite ester has the formula

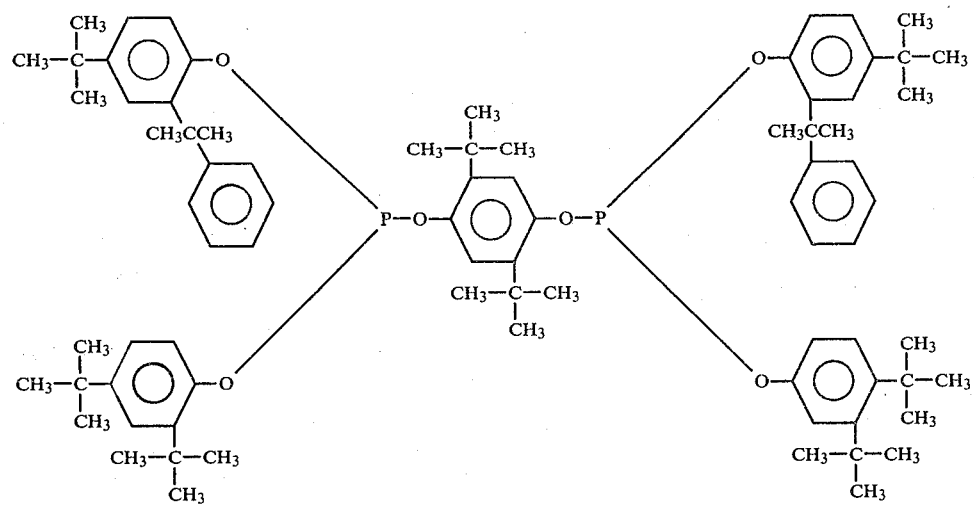
19. A synthetic resin composition according to claim 1 in which the polyphosphite ester has the formula
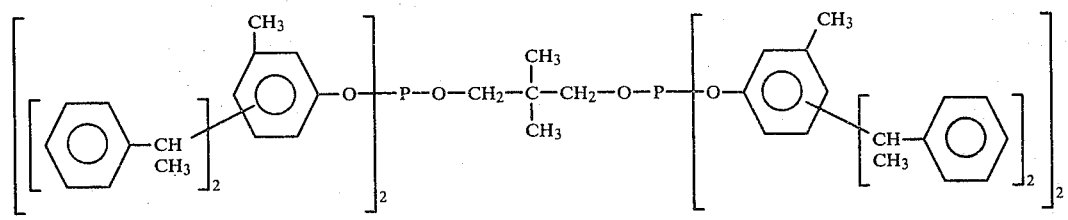
* * * * *